(12) United States Patent
Castells Boliart et al.

(10) Patent No.: US 8,569,507 B2
(45) Date of Patent: Oct. 29, 2013

(54) *N*-(2-OXO-1-PHENYLPIPERIDIN-3-YL)SULFONAMIDES FOR THE IDENTIFICATION OF BIOLOGICAL AND PHARMACOLOGICAL ACTIVITY

(75) Inventors: Josep Castells Boliart, Mollet Del Valles (ES); David Enrique Miguel Centeno, Mollet Del Valles (ES); Marta Pascual Gilabert, Mollet Del Valles (ES)

(73) Assignee: Institut Univ. De Ciencia I Technologia, S.A., Mollet del Valles (ES)

( * ) Notice: Subject to any disclaimer, the term of this patent is extended or adjusted under 35 U.S.C. 154(b) by 158 days.

(21) Appl. No.: 13/332,625

(22) Filed: Dec. 21, 2011

(65) Prior Publication Data

US 2012/0142930 A1 Jun. 7, 2012

Related U.S. Application Data

(63) Continuation-in-part of application No. PCT/IB2010/052856, filed on Jun. 23, 2010.

(30) Foreign Application Priority Data

Jun. 25, 2009 (ES) .................................. 200901515

(51) Int. Cl.
*A61K 31/535* (2006.01)
*C07D 215/36* (2006.01)
(52) U.S. Cl.
USPC .......................................... 546/172; 514/330
(58) Field of Classification Search
USPC ......................................................... 546/172
See application file for complete search history.

(56) References Cited

U.S. PATENT DOCUMENTS

| 6,939,973 | B1 | 9/2005 | Rebek, Jr. et al. |
| 7,126,006 | B2 | 10/2006 | Rebek, Jr. et al. |
| 2002/0183324 | A1 | 12/2002 | Jacobson et al. |
| 2004/0006062 | A1 | 1/2004 | Smallheer et al. |
| 2006/0287315 | A1* | 12/2006 | Rohrig et al. .............. 514/235.5 |
| 2012/0122708 | A1 | 5/2012 | Boliart et al. |
| 2012/0122709 | A1 | 5/2012 | Boliart et al. |
| 2012/0122710 | A1 | 5/2012 | Boliart et al. |
| 2012/0122920 | A1 | 5/2012 | Boliart et al. |
| 2012/0122950 | A1 | 5/2012 | Boliart et al. |
| 2012/0129888 | A1 | 5/2012 | Boliart et al. |
| 2012/0142930 | A1 | 6/2012 | Boliart et al. |
| 2012/0142936 | A1 | 6/2012 | Boliart et al. |
| 2012/0149909 | A1 | 6/2012 | Boliart et al. |

FOREIGN PATENT DOCUMENTS

| WO | 02102380 | 12/2002 |
| WO | 2004041776 | 5/2004 |
| WO | 2010/015204 | 12/2010 |

OTHER PUBLICATIONS

Goodman and Gilman (The Pharmacological Basis of Therapeutics, 8th ed, McGraw-Hill, Int. Ed. 1992, "Biotransformation of Drugs", p. 13-15).
Smallheer et al. (Bioorganic & Medicinal Chemistry Letters (2008), 18(7), 2428-2433).
Pravda, Z., et al., "Amino acids and peptides. XIII. Synthesis of L-proline from L-glutamic acid," Collect. Czechoslovak Chem. Comm., 1955, vol. 20, pp. 1-8.

* cited by examiner

*Primary Examiner* — John Mabry
(74) *Attorney, Agent, or Firm* — Barnes & Thornburg LLP

(57) ABSTRACT

Novel compounds are continually sought after to treat and prevent diseases and disorders. The invention relates to N-(2-oxo-1-phenylpiperidin-3-yl)sulfonamides useful for being biologically and pharmacologically screened, and to contribute to the exploration and identification of new lead molecules that are capable of modulating the functional activity of a biological target.

5 Claims, No Drawings

N-(2-OXO-1-PHENYLPIPERIDIN-3-YL)SULFONAMIDES FOR THE IDENTIFICATION OF BIOLOGICAL AND PHARMACOLOGICAL ACTIVITY

This application claims priority under 35 U.S.C. 365(c) from PCT/IB2010/052856, filed 23 Jun. 2010, the disclosure of which is incorporated by reference herein.

FIELD OF THE INVENTION

The field of the invention is medicinal chemistry. The invention relates to N-(2-oxo-1-phenylpiperidin-3-yl)sulfonamides useful for the identification of biological and pharmacological activity in drug discovery.

BACKGROUND OF THE INVENTION

Novel compounds are continually sought after to treat and prevent diseases and disorders. Pharmaceutical companies interested in owning new active molecules develop or purchase chemical compounds or libraries in order to screen their activity against a particular target, aiming at the identification of new industrially useful products.

Therefore, there is a market of customer companies for which the acquisition of novel chemical compounds, not already biologically explored, is a key issue. And for the companies whose core business is the design and preparation of chemical compounds or chemical libraries, their commercialization has a clear industrial interest.

Although many research groups work to find novel compounds to be used in the treatment of known or novel diseases, the number of active new chemical entities in the market doesn't grow in the same extension. Over the past few years, there has been a progressive reduction in the number of medicines entering the market mainly due to the more stringent regulatory requirements that have raised the bar on safety and efficacy of new drugs.

The compounds described in this invention are useful for contributing to the exploration of the chemical space, for incrementing the structural diversity of valuable molecules in the pharmaceutical sector and for incrementing the elements of structural recognition in order to study their interaction with or modulation of targets of pharmaceutical or medicinal chemistry interest. For instance, the molecules may be therapeutically useful as anti-inflammatory or anticoagulation agents, among many other applications.

Compounds described in this invention are useful for being biologically and pharmaceutically explored, and therefore to contribute in the research and identification of new drug leads exhibiting the ability of target modulation, since these molecules are sources of chemical diversity not currently explored. The compounds of the present invention may be explored by means of any known method of biological screening. These methods comprise, but are not limited to, receptor affinity assays, ELISA assays, "southern", "western" and "northern blot", and competitive binding assays.

U.S. Pat. No. 7,126,006 B2 (The Scripps Research Institute) describes glycoluryl type molecules as scaffolds in the preparation of combinatorial libraries.

U.S. Pat. No. 6,939,973 B1 (The Scripps Research Institute) describes glycoluryl type molecules as scaffolds in the preparation of combinatorial libraries.

Smallheer et al. (Bioorganic & Medicinal Chemistry Letters (2008), 18(7), 2428-2433) disclose a series of sulfonamidolactams useful as coagulation Factor Xa inhibitors.

WO2004041776 (Bristol-Myers Squibb Company) discloses certain sulfonylamino-valerolactams that can be used as inhibitors of trypsin-like serine proteases, specifically factor Xa.

WO2002102380 (Bristol-Myers Squibb Pharma. Co.) discloses monocyclic and bicyclic carbocycles and heterocycles active as factor Xa inhibitors.

The search for novel drug lead compounds for drug discovery is a difficult task that has traditionally required the use of hundreds of thousands of compounds to reach a successful molecule, mainly due to the fact that drug discovery was driven by random screening and the chemical and biological intuition.

However, integrated approaches combining structural knowledge from conformationally constrained small peptides and parallel synthesis of small molecules are particularly well suited for the shortening of the time-consuming drug discovery process.

Compounds of formula (I) have been designed using computational techniques such as virtual library screening based on pharmacophore search. Virtual (database) screening (VS) is an important component of the computer-based search of novel lead compounds. The primary VS premise is to screen a database of molecules computationally using structural descriptors that relate in some way to potential biological activity. A subset of database molecules found to match these descriptors can then be selected for subsequent biological analysis. In terms of novel lead discovery, pharmacophore searching is one of the most widely applied VS methods.

Compounds of formula (I) are not an arbitrary selection of a vast amount of molecules. On the contrary, they have been designed using as starting point a pharmacophore for at least BK antagonism. In this context, a pharmacophore is defined as a critical arrangement of molecular fragments or features creating a necessary, although not sufficient, condition for biological activity and receptor affinity.

In order to improve the success of molecular bioactive conformations, applicants have defined the structure of compounds of formula (I) using a pharmacophore based on Hoe 140, the most potent peptide antagonist of brakykinin (BK, sequence: D-Arg$^0$-Arg$^1$-Pro$^2$-Hyp$^3$-Gly$^4$-Thi$^5$-Ser$^6$-D-Tic$^7$-Oic$^8$-Arg$^9$ (Hyp, hydroxyproline; Thi, β-(2-thienyl)-alanine; Tic, 1,2,3,4-tetrahydroisoquinoline-3-carboxylic acid; Oic, (2S,3aS,7aS)-octahydroindole-2-carboxylic acid). The pharmacophore for BK antagonism has been obtained from a conformational search using an iterative simulated annealing procedure. Corcho, F J. Computational Studies on the Structure and Dynamics of Bioactive Peptides, PhD Thesis, 2004.

In conclusion, all compounds of formula (I) exhibit at least Hoe 140 pharmacophore fulfillment, and therefore they share specific characteristics for receptor affinity critical in the search of novel bioactive molecules.

DESCRIPTION OF THE INVENTION

The present invention concerns the compounds represented by formula (I)

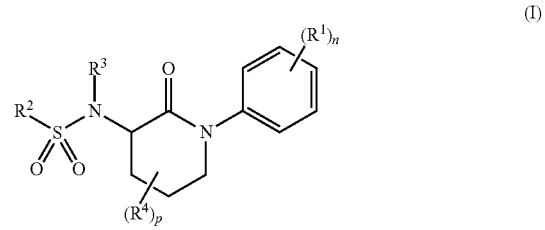

and the salts and stereoisomers thereof, wherein $R^1$ is hydrogen, hydroxy, nitro, cyano, carboxyl, $C_{1-6}$alkyl, $C_{1-6}$alkoxy, $C_{1-6}$alkoxy-$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy, aryl, Het;

$R^2$ is $C_{3-7}$cycloalkyl optionally substituted with $C_{1-6}$alkyl; $C_{1-6}$alkyl optionally substituted with $C_{3-7}$cycloalkyl, aryl or Het; $C_{2-6}$alkenyl optionally substituted with $C_{3-7}$cycloalkyl, aryl or Het; aryl; Het; or —$NR^{4a}R^{4b}$, wherein $R^{4a}$ and $R^{4b}$ are, each independently, $C_{1-6}$alkyl, or $R^{4a}$ and $R^{4b}$ together with the nitrogen to which they are attached form a 5- or 6-membered saturated heterocyclic ring;

$R^3$ is hydrogen, $C_{1-6}$alkylcarbonyl, $C_{1-6}$alkyl optionally substituted with aryl, $C_{1-6}$alkoxy$C_{1-6}$alkyl, or $C_{3-7}$cycloalkyl, $C_{1-6}$alkyl optionally substituted with Het;

$R^4$ is hydrogen, hydroxy, halo, nitro, cyano, carboxyl, $C_{1-6}$alkyl, $C_{1-6}$alkoxy, $C_{1-6}$alkoxy$C_{1-6}$alkyl or $C_{3-7}$cycloalkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy, $C_{1-6}$alkyl optionally substituted with aryl or Het; $C_{3-7}$cycloalkyl optionally substituted with $C_{1-6}$alkyl; $C_{1-6}$alkyl optionally substituted with $C_{3-7}$cycloalkyl, aryl or Het; $C_{2-6}$alkenyl optionally substituted with $C_{3-7}$cycloalkyl, aryl or Het; aryl; Het; or —$NR^{4a}R^{4b}$, wherein $R^{4a}$ and $R^{4b}$ are, each independently, $C_{1-6}$alkyl, or $R^{4a}$ and $R^{4b}$ together with the nitrogen to which they are attached form a 5- or 6-membered saturated heterocyclic ring;

n is one, two, three, four or five;

p is one, two, three, four or five, independently of n;

each aryl as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy;

each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$ alkoxy$C_{1-6}$alkyl, $C_{1-6}$ alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

The invention further relates to methods for the preparation of the compounds of formula (I), the N-oxides, addition salts, quaternary amines, metal complexes, and stereochemically isomeric forms thereof, their intermediates, and the use of the intermediates in the preparation of the compounds of formula (I).

The invention relates to the compounds of formula (I) per se, the N-oxides, addition salts, quaternary amines, metal complexes, and stereochemically isomeric forms thereof, for use as lead compounds to be biologically and pharmacologically explored in the search and identification of new drugs.

As used in the foregoing and hereinafter, the following definitions apply unless otherwise noted.

The term halo is generic to fluoro, chloro, bromo and iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro $C_{1-6}$alkyl groups, which are $C_{1-6}$alkyl groups wherein all hydrogen atoms are replaced by fluorine atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

$C_{3-7}$cycloalkyl is generic to cyclopropyl, cyclobutyl, cyclopentyl, cyclohexyl and cycloheptyl.

$C_{1-6}$alkoxy means $C_{1-6}$alkyloxy wherein $C_{1-6}$alkyl is as defined above.

It should be noted that the radical positions on any molecular moiety used in the definitions may be anywhere on such moiety as long as it is chemically stable.

Radicals used in the definitions of the variables include all possible positional isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, is meant to include the compounds of formula (I), each and any of the subgroups thereof, N-oxides, addition salts, quaternary amines, metal complexes, and stereochemically isomeric forms.

The present disclosure also includes the prodrugs of compounds of formula (I).

One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) may have one or more centers of chirality and may exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their N-oxides, salts, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides, and phosphates, such that the resulting in vivo biotransformation product of the derivative is the active drug as defined in the compounds of formula (I). The reference by Goodman and Gilman (The Pharmacological Basis of Therapeutics, 8th ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolyzed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

One embodiment of the present invention concerns compounds of formula (I) or of any subgroup of compounds of formula (I), wherein one or more of the following conditions apply:

$R^1$ is hydrogen, hydroxy, nitro, cyano, carboxyl, $C_{1-6}$alkyl, $C_{1-6}$alkoxy, $C_{1-6}$alkoxy-$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy, aryl, Het;

$R^2$ is $C_{3-7}$cycloalkyl optionally substituted with $C_{1-6}$alkyl; $C_{1-6}$alkyl optionally substituted with $C_{3-7}$cycloalkyl, aryl or Het; $C_{2-6}$alkenyl optionally substituted with $C_{3-7}$cycloalkyl, aryl or Het; aryl; Het; or —$NR^{4a}R^{4b}$, wherein $R^{4a}$ and $R^{4b}$ are, each independently, $C_{1-6}$alkyl, or $R^{4a}$ and $R^{4b}$ together with the nitrogen to which they are attached form a 5- or 6-membered saturated heterocyclic ring;

$R^3$ is hydrogen, $C_{1-6}$alkylcarbonyl, $C_{1-6}$alkyl optionally substituted with aryl, $C_{1-6}$alkoxy$C_{1-6}$alkyl, or $C_{3-7}$cycloalkyl, $C_{1-6}$alkyl optionally substituted with Het;

$R^4$ is hydrogen;

n is one, two, three, four or five;

p is one;

each aryl as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy;

each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

Another embodiment of the present invention concerns compounds of formula (I) or of any subgroup of compounds of formula (I), wherein one or more of the following conditions apply:

$R^1$ is hydrogen or $C_{1-6}$alkyl;

$R^2$ is $C_{1-6}$alkyl optionally substituted with $C_{3-7}$cycloalkyl, aryl or Het; $C_{2-6}$alkenyl optionally substituted with $C_{3-7}$cycloalkyl, aryl or Het; aryl; or Het;

$R^3$ is hydrogen, $C_{1-6}$alkyl or carboxyl;

$R^4$ is hydrogen;

n is one or two;

p is one;

each aryl as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy;

each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

One embodiment of the present invention concerns compounds of formula (I) or of any subgroup of compounds of formula (I), wherein one or more of the following conditions apply:

$R^1$ is hydrogen;

$R^2$ is $C_{2-6}$alkenyl optionally substituted with aryl or Het; aryl; or Het;

$R^3$ is hydrogen;

$R^4$ is hydrogen;

n is one or two;

p is one;

each aryl as a group or part of a group is phenyl or naphthalenyl, each optionally substituted with one or two substituents selected from halo, amino, mono- or di$C_{1-6}$alkylamino, and polyhalo$C_{1-6}$alkyl;

each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one or two substituents each independently selected from the group consisting of halo and polyhalo$C_{1-6}$alkyl.

The compounds of the present invention may be prepared according to the procedures described hereinafter, which are meant to be applicable for as well the racemates, stereochemically pure intermediates or end products, or any stereoisomeric mixtures. The racemates or stereochemical mixtures may be separated into stereoisomeric forms at any stage of the synthesis procedures.

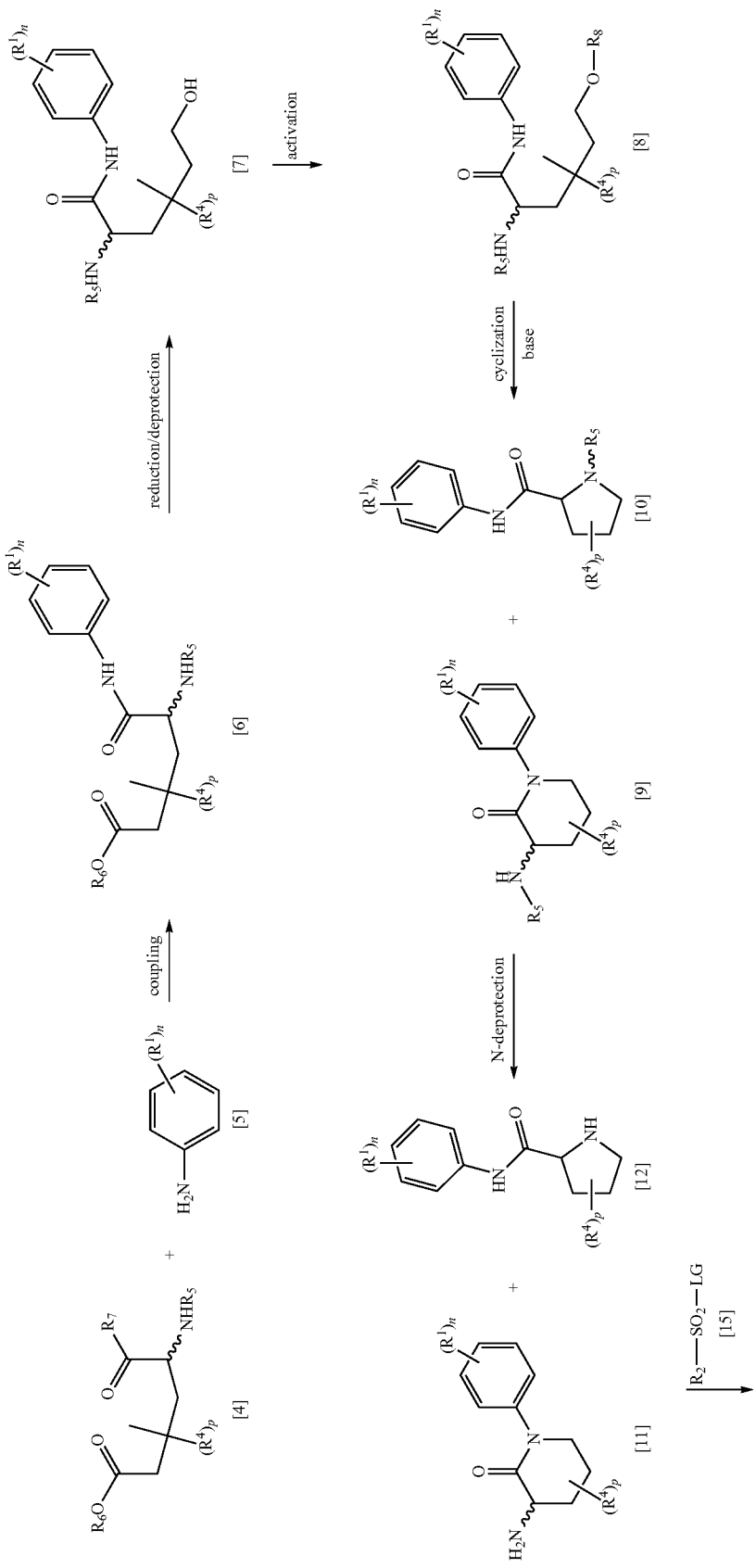

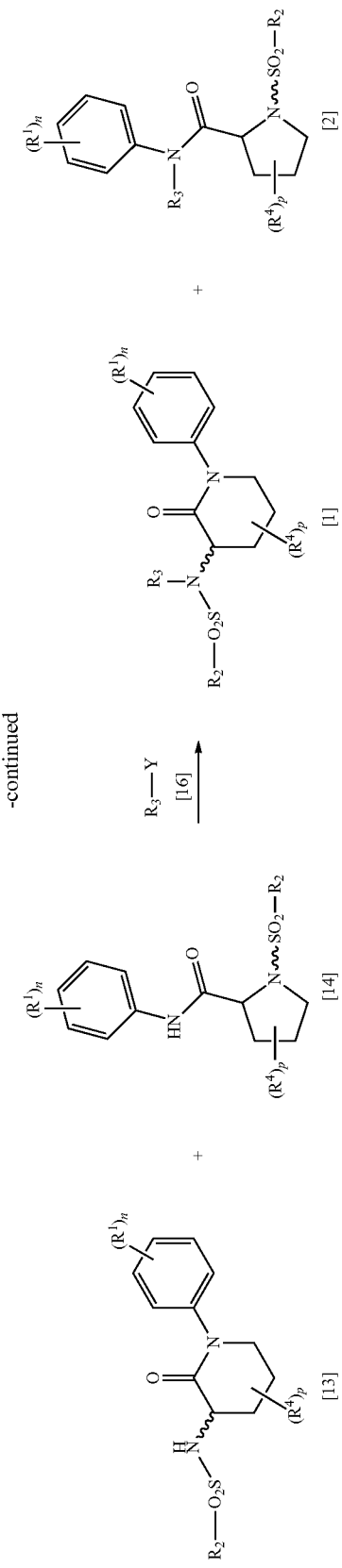

As shown in the above scheme 1, coupling of a compound of formula [4] with the primary amine compound of formula [5] gives the amide derivative compound of formula [6]. The coupling reaction occurs in an organic solvent, such as a chlorinated solvent, preferably dichloromethane, 1,2-dichloroethane or chloroform, at a temperature preferably between −10° C. and 40° C., more preferably between 0° C. and 25° C. Compound of formula [4] comprises a group —CO—$R_7$ in the form of an activated carboxyl derivative, such as acid chlorides, anhydrides, or active esters such as O-acylisoureas or acyloxyphosphonium derivatives. In a particular embodiment the carbonyl compound is carboxylic acid, the carboxyl activate derivative is O-acylisourea and the activating group is a carbodiimide coupling reagent such as dicyclohexylcarbodiimide (DCC), while in another the coupling group is diisopropylcarbodiimide (DIPC).

The corresponding reduction or deprotection reaction of compound [6] yields the alcohol of formula [7]. In a particular embodiment, $R_6$ group is a benzyl protecting group, and the deprotection reaction comprises the chemoselective reduction of the metal hydride with a reductive agent such as $NaBH_4$ or $Ca(BH_4)_2$ in a polar protic solvent, such as ethanol or 2-propanol at a temperature preferably between −10° C. and 25° C., more preferably between 0° C. and 10° C.

The activation of compound [7] to furnish compound of formula [8] occurs by means of sulfonyl halides, preferably para-toluenesulfonyl halides, methanesulfonyl halides or trifluoromethanesulfonyl halides, in the presence of an organic aliphatic or aromatic base, such as pyridine, imidazole, or triethylamine. In a particular embodiment, $R_8$ group is a methanesulfonyl activating group, and the reaction occurs in a chlorinated solvent, preferably dichloromethane, 1,2-dichloroethane or chloroform, in anhydrous or non anhydrous conditions, at a temperature preferably between −10° C. and 40° C., more preferably between 0° C. and 25° C.

Treatment of compound [8] under cyclisation conditions yields the lactam compound of formula [9] and the pyrrolidine compound of formula [10]. The reaction occurs in the presence of an inorganic or organic base, such as sodium hydride, potassium tert-butoxide or lithium diisopropylamide, at a temperature preferably between −78° C. and 60° C., more preferably between −40° C. and 0° C. The reaction solvent is a polar aprotic solvent, preferably acetonitrile, tetrahydrofuran, dimethylformamide, or dimethylsulfoxide.

The N-deprotection of compounds [9] and [10] yields compounds of formulae [11] and [12], respectively where $R_5$ is an amino protecting group, carbamate, urea-type derivative, amide, cyclic imide, alkyl, aryl, imine, enamine or heteroatom. In a particular embodiment, the protecting group is tert-butoxycarbonyl group and the deprotecting agent is trifluoroacetic acid in a chlorinated solvent, preferably dichloromethane, 1,2-dichloroethane or chloroform, at a trifluoroacetic acid composition preferably between 5% and 90%, more preferably between 15% and 70%, at a temperature preferably between 0° C. and 45° C., more preferably between 10° C. and 30° C.

The substitution reaction of [11] or [12] with compounds of formula $R_2$—$SO_2$-LG, where LG means "leaving group", being said LG group preferably an halogen atom, more preferably bromine or chlorine, yields the corresponding substituted sulfonamides of formula [13] and [14], respectively. The reaction solvent is a chlorinated solvent, preferably dichloromethane, 1,2-dichloroethane or chloroform, or a polar aprotic solvent, preferably acetonitrile, tetrahydrofuran, or dimethylformamide, at a temperature preferably between 0° C. and 40° C., more preferably between 10° C. and 25° C.

Under substitution or coupling conditions with compounds of formula $R_3$—Y, where Y means "leaving group" in substitution reaction and "activating group" in coupling reactions, being said Y preferably is a halogen atom, more preferably bromine or chlorine in substitution reaction, or an activated carboxyl derivative in coupling reactions, compounds [13] and [14] are converted to the final compounds of formula [1] and [2], respectively. The reaction solvent is a hydrous or anhydrous polar aprotic solvent, preferably acetonitrile, tetrahydrofuran, or dimethylformamide, at a temperature preferably between −78° C. and 60° C., more preferably between −78° C. and 25° C.

Both racemic as well as pure enantiomers of [1] and [2] can be accessed by this approach depending on the stereochemical integrity of the starting material.

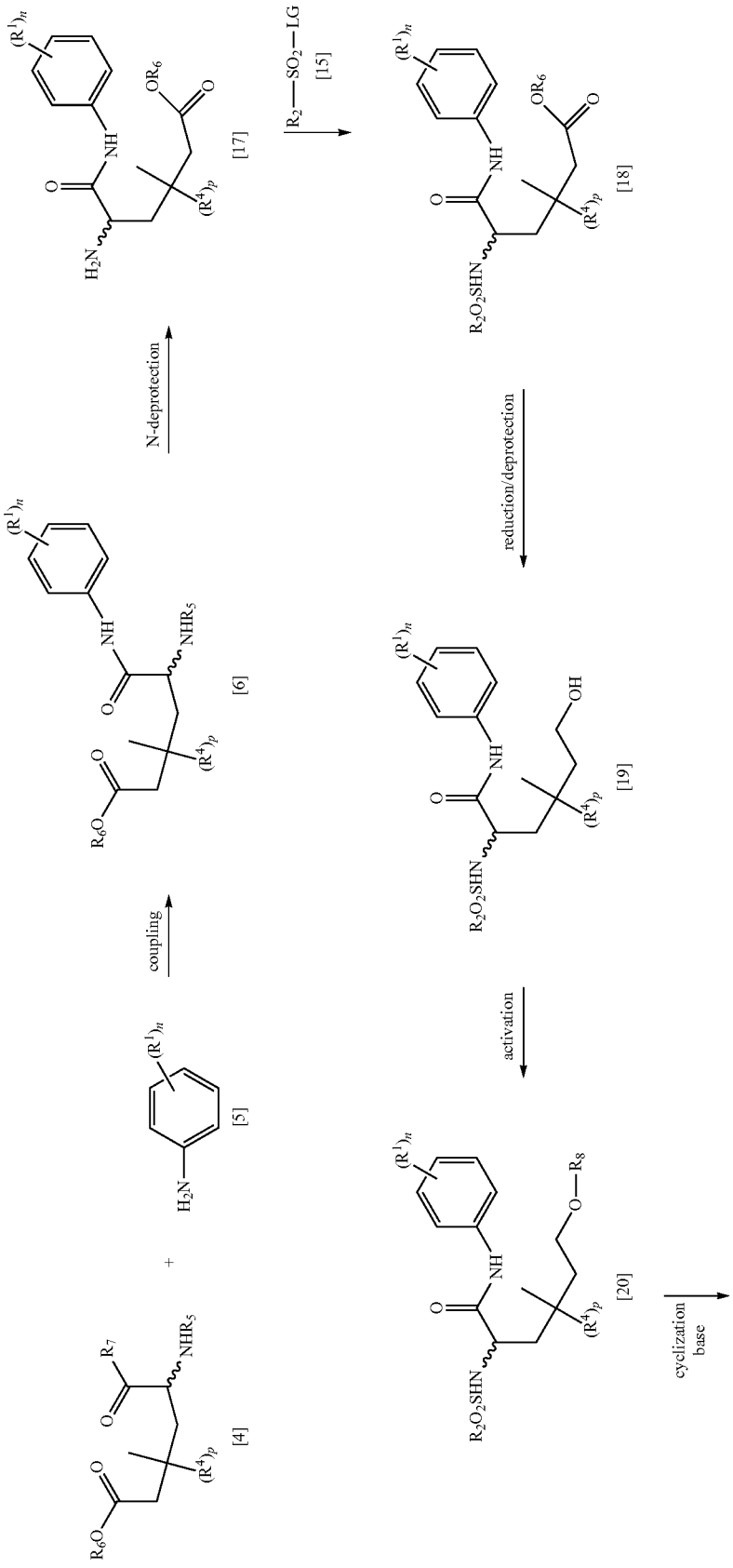

-continued
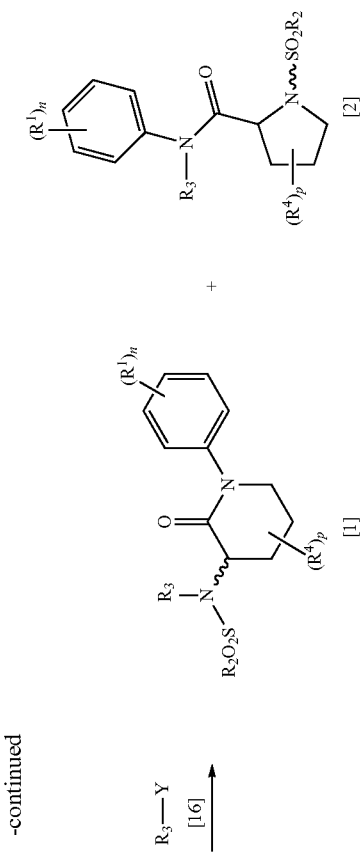
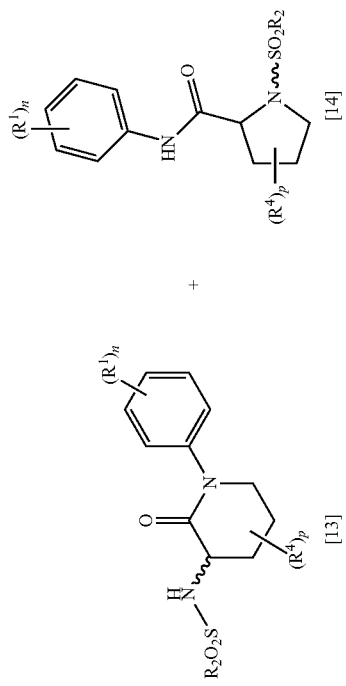

Alternatively, the compounds of formula [1] or [2] can be prepared by the approach as shown in scheme 2. According to scheme 2, coupling of a compound of formula [4] with the compound of formula [5] gives the amide derivative compound of formula [6]. The coupling reaction occurs in an organic solvent, such as a chlorinated solvent, preferably dichloromethane, 1,2-dichloroethane or chloroform, at a temperature preferably between −10° C. and 40° C., more preferably between 0° C. and 25° C. Compound of formula [4] comprises a group —CO—R$_7$ in the form of an activated carboxyl derivative, such as acid chlorides, anhydrides, or active esters such as O-acylisoureas or acyloxyphosphonium derivatives. In a particular embodiment the carbonyl compound is carboxylic acid, the carboxyl activate derivative is O-acylisourea and the activating group is a carbodiimide coupling reagent such as dicyclohexylcarbodiimide (DCC), while in another the coupling group is diisopropylcarbodiimide (DIPC).

The N-deprotection of compound [6] yields compounds of formula [17]. In a particular realization the protecting group is tert-butoxycarbonyl group and the deprotecting agent is trifluoroacetic acid in a chlorinated solvent, preferably dichloromethane, 1,2-dichloroethane or chloroform, at a trifluoroacetic acid composition preferably between 5% and 90%, more preferably between 15% and 70%, at a temperature preferably between 0° C. and 45° C., more preferably between 10° C. and 30° C.

The coupling reaction of [17] with compounds of formula R$_2$—SO$_2$-LG, where LG means "leaving group", being said LG group preferably an halogen atom, more preferably bromine or chlorine, yields the corresponding substituted sulfonamide of formula [18]. The reaction solvent is a chlorinated solvent, preferably dichloromethane, 1,2-dichloroethane or chloroform, or a polar aprotic solvent, preferably acetonitrile, tetrahydrofuran, or dimethylformamide, at a temperature preferably between 0° C. and 40° C., more preferably between 10° C. and 25° C.

The corresponding reduction or deprotection reaction of compound [18] yields the alcohol of formula [19]. In a particular embodiment, R$_6$ group is a benzyl protecting group, and the deprotection reaction comprises the chemoselective reduction of the metal hydride with an reductive agent such as NaBH$_4$ or Ca(BH$_4$)$_2$ in a polar protic solvent, such as ethanol or 2-propanol at a temperature preferably between −10° C. and 25° C., more preferably between 0° C. and 10° C.

Activation of compound [19] furnishes compound of formula [20]. The reaction occurs by means of sulfonyl halides, preferably para-toluenesulfonyl halides, methanesulfonyl halides or trifluoromethanesulfonyl halides, in the presence of an organic aliphatic or aromatic base, such as pyridine, imidazole, or triethylamine. The reaction occurs in a chlorinated solvent, preferably dichloromethane, 1,2-dichloroethane or chloroform, in anhydrous or non anhydrous conditions, at a temperature preferably between −10° C. and 40° C., more preferably between 0° C. and 25° C.

Treatment of compound [20] under cyclisation conditions yields the lactam compound of formula [13] and the pyrrolidine compound of formula [14]. The reaction occurs in the presence of an inorganic or organic base, such as sodium hydride, potassium tert-butoxide or lithium diisopropylamide, at a temperature preferably between −78° C. and 60° C., more preferably between −40° C. and 0° C. The reaction solvent is a polar aprotic solvent, preferably acetonitrile, tetrahydrofuran, dimethylformamide, or dimethylsulfoxide.

Under substitution or coupling conditions with compounds of formula R$_3$—Y, where Y means "leaving group" in substitution reaction and "activating group" in coupling reactions, being said Y preferably is a halogen atom, more preferably bromine or chlorine in substitution reaction, or an activated carboxyl derivative in coupling reactions, compounds [13] and [14] are converted to the final compounds of formula [1] and [2], respectively. The reaction solvent is a hydrous or anhydrous polar aprotic solvent, preferably acetonitrile, tetrahydrofuran, or dimethylformamide, at a temperature preferably between −78° C. and 60° C., more preferably between −78° C. and 25° C. Both racemic as well as pure enantiomers of [1] and [2] can be accessed by this approach depending on the stereochemical integrity of the starting material.

The compounds of the present invention may be used, biologically and pharmacologically explored in the search and identification of new lead compounds in the drug discovery process. The abovementioned use comprises the compounds of formula (I)

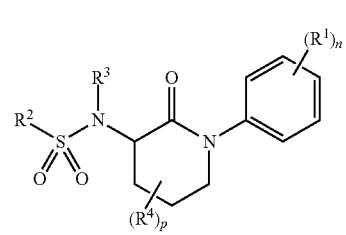

and the salts and stereoisomers thereof, wherein

R$^1$ is hydrogen, hydroxy, nitro, cyano, carboxyl, C$_{1-6}$alkyl, C$_{1-6}$alkoxy, C$_{1-6}$alkoxy-C$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, aryl, Het;

R$^2$ is C$_{3-7}$cycloalkyl optionally substituted with C$_{1-6}$alkyl; C$_{1-6}$alkyl optionally substituted with C$_{3-7}$cycloalkyl, aryl or Het; C$_{1-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

R$^3$ is hydrogen, C$_{1-6}$alkylcarbonyl, C$_{1-6}$alkyl optionally substituted with aryl, C$_{1-6}$alkoxyC$_{1-6}$alkyl, or C$_{3-7}$cycloalkyl, C$_{1-6}$alkyl optionally substituted with Het;

R$^4$ is hydrogen, hydroxy, halo, nitro, cyano, carboxyl, C$_{1-6}$alkyl, C$_{1-6}$alkoxy, C$_{1-6}$alkoxyC$_{1-6}$alkyl or C$_{3-7}$cycloalkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, C$_{1-6}$alkyl optionally substituted with aryl or Het; C$_{3-7}$cycloalkyl optionally substituted with C$_{1-6}$alkyl; C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

n is one, two, three, four or five;

p is one, two, three, four or five, independently of n;

each aryl as a group or part of a group is phenyl or naphthalenyl, each optionally substituted with one, two or three substituents selected from halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy;

each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

The present invention comprises the use of the compounds of formula (I), their salts and stereoisomers used for being biologically and pharmacologically explored in the search and identification of new lead compounds in the drug discovery process. The abovementioned use comprises the compounds of formula (I)

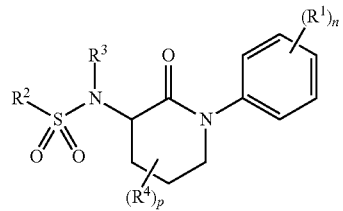

(I)

and the salts and stereoisomers thereof, wherein
$R^1$ is hydrogen, halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy, aryl, Het;
$R^2$ is $C_{3-7}$cycloalkyl optionally substituted with $C_{1-6}$alkyl; $C_{1-6}$alkyl optionally substituted with $C_{3-7}$cycloalkyl, aryl or Het; $C_{2-6}$alkenyl optionally substituted with $C_{3-7}$cycloalkyl, aryl or Het; aryl; Het; or —$NR^{4a}R^{4b}$, wherein $R^{4a}$ and $R^{4b}$ are, each independently, $C_{1-6}$alkyl, or $R^{4a}$ and $R^{4b}$ together with the nitrogen to which they are attached form a 5- or 6-membered saturated heterocyclic ring;
$R^3$ is hydrogen, $C_{1-6}$alkylcarbonyl, $C_{1-6}$alkyl optionally substituted with aryl, $C_{1-6}$alkoxy$C_{1-6}$alkyl, or $C_{3-7}$cycloalkyl, $C_{1-6}$alkyl optionally substituted with Het;
$R^4$ is hydrogen;
n is one, two, three, four or five;
p is one;
each aryl as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy;
each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

As such, in one embodiment, the present invention relates to a process for preparing a compound of formula (I) as described herein, said process comprising
a) reacting in a suitable medium compound of formula (II) with a compound of

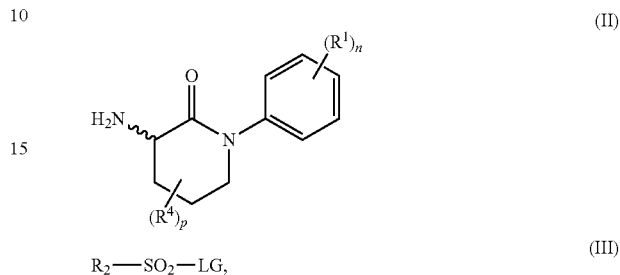

and
b) optionally further reacting in a suitable medium the product of step a) with $R_3$—Y;
wherein
$R_1$, $R_2$, $R_3$, $R_4$, n and p have the same definition as provided herein;
LG is a leaving group;
Y is an activating group in coupling reactions or a leaving group in substitution reactions.

The suitable medium of the reaction in step a) is anhydrous or non anhydrous chlorinated solvent, preferably dichloromethane, 1,2-dichloroethane or chloroform, or a hydrous or anhydrous polar aprotic solvent, preferably acetonitrile, tetrahydrofuran, or dimethylformamide, at a temperature preferably between 0° C. and 40° C., more preferably between 0° C. and 25° C.

The suitable medium of the reaction in step b) is in the presence of an inorganic or organic base, such as sodium hydride, potassium tert-butoxide or lithium diisopropylamide, at a temperature preferably between −78° C. and 60° C., more preferably between −78° C. and 25° C. The reaction solvent is a polar aprotic solvent, preferably acetonitrile, tetrahydrofuran, dimethylformamide, or dimethylsulfoxide.

The term "leaving group" is preferably a halogen atom, more preferably bromine or chlorine.

The term "activating group" is preferably but not limited to a carboxyl activant in coupling reactions, preferably in the form of an acid chloride, anhydride, or active esters, such as O-acylisoureas or acyloxyphosphonium derivatives.

Compounds of formula (I) may be converted into each other following art-known functional group transformation reactions. For example, amino groups may be N-alkylated, nitro groups reduced to amino groups, a halo atom may be exchanged for another halo.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

One embodiment of the present invention concerns compounds of formula (IV) or any subgroup of compounds of formula (IV), and the salts and stereoisomers thereof, wherein one or more of the following conditions apply

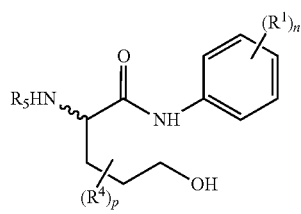

(IV)

wherein
R$^1$ is hydrogen, hydroxy, nitro, cyano, carboxyl, C$_{1-6}$alkyl, C$_{1-6}$alkoxy, C$_{1-6}$alkoxy-C$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, aryl, Het;

R$^4$ is hydrogen, hydroxy, halo, nitro, cyano, carboxyl, C$_{1-6}$alkyl, C$_{1-6}$alkoxy, C$_{1-6}$alkoxyC$_{1-6}$alkyl or C$_{3-7}$cycloalkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, C$_{1-6}$alkyl optionally substituted with aryl or Het; C$_{3-7}$cycloalkyl optionally substituted with C$_{1-6}$alkyl; C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

R$_5$ is an amino protecting group, in the form of carbamate, urea-type derivative, amide, cyclic imide, alkyl, aryl, imine, enamine or heteroatom;

n is one, two, three, four or five;

p is one, two, three, four or five, independently of n;

The invention further relates to compounds of formula (IV) per se, the N-oxides, addition salts, quaternary amines, metal complexes, and stereochemically isomeric forms thereof, for use as synthetic intermediates in the preparation of compounds of formula (I).

One embodiment of the present invention concerns compounds of formula (V) or any subgroup of compounds of formula (V), and the salts and stereoisomers thereof, wherein one or more of the following conditions apply

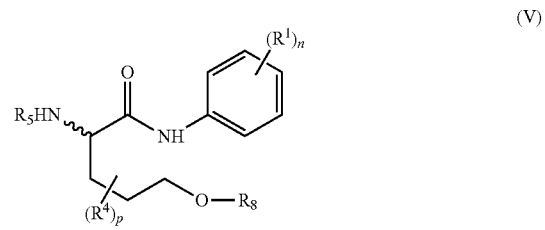

(V)

wherein
R$^1$ is hydrogen, hydroxy, nitro, cyano, carboxyl, C$_{1-6}$alkyl, C$_{1-6}$alkoxy, C$_{1-6}$alkoxy-C$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, aryl, Het;

R$^4$ is hydrogen, hydroxy, halo, nitro, cyano, carboxyl, C$_{1-6}$alkyl, C$_{1-6}$alkoxy, C$_{1-6}$alkoxyC$_{1-6}$alkyl or C$_{3-7}$cycloalkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, C$_{1-6}$alkyl optionally substituted with aryl or Het; C$_{3-7}$cycloalkyl optionally substituted with C$_{1-6}$alkyl; C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

R$_5$ is an amino protecting group, in the form of carbamate, urea-type derivative, amide, cyclic imide, alkyl, aryl, imine, enamine or heteroatom;

R$_8$ is an hydroxy activating group, preferably in the form of a sulfonate ester, para-toluenesulfonyl, methanesulfonyl or trifluoromethanesulfonyl;

n is one, two, three, four or five;

p is one, two, three, four or five, independently of n;

The invention further relates to compounds of formula (V) per se, the N-oxides, addition salts, quaternary amines, metal complexes, and stereochemically isomeric forms thereof, for use as synthetic intermediates in the preparation of compounds of formula (I).

One embodiment of the present invention concerns compounds of formula (VI) or any subgroup of compounds of formula (VI), and the salts and stereoisomers thereof, wherein one or more of the following conditions apply:

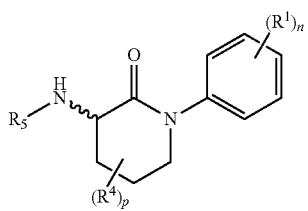

wherein
$R^1$ is hydrogen, hydroxy, nitro, cyano, carboxyl, $C_{1-6}$alkyl, $C_{1-6}$alkoxy, $C_{1-6}$alkoxy-$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy, aryl, Het;

$R^4$ is hydrogen, hydroxy, halo, nitro, cyano, carboxyl, $C_{1-6}$alkyl, $C_{1-6}$alkoxy, $C_{1-6}$alkoxy$C_{1-6}$alkyl or $C_{3-7}$cycloalkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy, $C_{1-6}$alkyl optionally substituted with aryl or Het; $C_{3-7}$cycloalkyl optionally substituted with $C_{1-6}$alkyl; $C_{1-6}$alkyl optionally substituted with $C_{3-7}$cycloalkyl, aryl or Het; $C_{2-6}$alkenyl optionally substituted with $C_{3-7}$cycloalkyl, aryl or Het; aryl; Het; or —$NR^{4a}R^{4b}$, wherein $R^{4a}$ and $R^{4b}$ are, each independently, $C_{1-6}$alkyl, or $R^{4a}$ and $R^{4b}$ together with the nitrogen to which they are attached form a 5- or 6-membered saturated heterocyclic ring;

$R_5$ is an amino protecting group, carbamate, urea-type derivative, amide, cyclic imide, alkyl, aryl, imine, enamine or heteroatom;

n is one, two, three, four or five;
p is one, two, three, four or five, independently of n;

The invention further relates to compounds of formula (VI) per se, the N-oxides, addition salts, quaternary amines, metal complexes, and stereochemically isomeric forms thereof, for use as synthetic intermediates in the preparation of compounds of formula (I).

EXAMPLES

The following examples are intended to illustrate the present invention and not to limit it thereto.

Example 1

Preparation of Intermediate [6a]: Benzyl 4-(tert-butoxycarbonyl-amino)-5-oxo-5-(phenylamino)Pentanoate

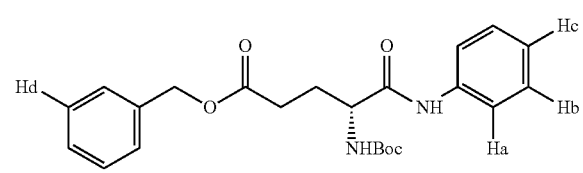

To a stirred solution of Boc-L-glutamic acid 5-benzyl ester [4a] (41 g, 122 mmol) in anhydrous $CH_2Cl_2$ (45 ml) at 0° C., was added during 15 minutes a solution of DCC (30.1 g, 146 mmol) in anhydrous $CH_2Cl_2$ (45 ml). The resulting white solid was sonicated. After that, anhydrous aniline was added dropwise to the reaction mixture over 10 minutes at 0° C. (11.1 ml, 122 mmol). The mixture was stirred at room temperature for 40 minutes and filtered through Celite® to remove insoluble material. The resulting liquid was evaporated to dryness and chromatographically purified, yielding the desired product (47.2 g, 94%).

$^1$H-NMR (400 MHz, CDCl$_3$): δ: 8.40 (br, 1H, CONHPh), 7.43 (d, 2H, J=7.7 Hz, 2H$_a$), 7.28 (d, 2H, J=7.7 Hz, H$_b$), 7.20 (m, 5H, 5×H$_d$), 7.02 (t, 1H, J=7.4 Hz, H$_c$), 5.35 (d, 1H, J=7.8 Hz, CHNHBoc), 5.04 (d, 2H, J=2.6 Hz, BnOCH$_2$), 4.26 (sa, 1H, CH$_2$CHNHBoc), 2.60-2.52 (mc, 1H, 1×OCOCH$_2$CH$_2$), 2.46-2.38 (mc, 1H, 1×OCOCH$_2$CH$_2$), 2.21-2.12 (mc, 1H, 1×OCOCH$_2$CH$_2$), 1.99-1.90 (mc, 1H, 1×OCOCH$_2$CH$_2$), 1.40 (s, 9H, NHCO$_2$C(CH$_3$)$_3$) ppm.

MS: Positive mode [M+Na]$^+$=435.

MS: Negative mode [M+2H$_2$O−H]$^-$=447.

CAS nr: [126349-57-3]

Example 2

Preparation of Intermediate [7a]: Tert-butyl 5-hydroxy-1-oxo-(phenylamino)Pentan-2-ylcarbamate

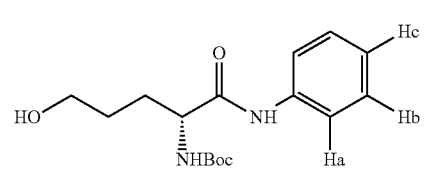

To a stirred suspension of NaBH$_4$ (12.5 g, 342 mmol) in 200 ml EtOH at 0° C. was added crushed CaCl$_2$ (19.9 g, 171 mmol) in portions during 15 min. After that, compound [6a] (35.2 g, 85.8 mmol) was added in portions during 10 minutes. The solution was stirred for 3.5 h, warming to room temperature. The crude was neutralized at 0° C. using HCl 0.1 M, and the aqueous phase was extracted in AcOEt. The organic phase was washed using saturated NaCl, dried over anhydrous Na$_2$SO$_4$ and evaporated to dryness. The resulting oil residue was chromatographically purified over SiO$_2$ in Hexane/AcOEt (40:60), furnishing the desired product (17.4 g, 65%).

$^1$H-NMR (300 MHz, CDCl$_3$), δ: 8.85 (br, 1H, CONHPh), 7.50 (dd, 2H, J$_1$=8.7 Hz, J$_2$=1.2 Hz, 2×H$_a$), 7.27 (dd, 2H, J$_1$=8.4 Hz, J$_2$=7.8 Hz, 2×H$_b$), 7.08 (t, 1H, J$_r$=7.2 Hz, H$_c$), 5.57 (sa, 1H, J=5.7 Hz, CHNHBoc), 4.41 (br, 1H, J=5.7 Hz, CHNHBoc), 3.74 (m, 2H, CH$_2$OH), 2.94 (br, 1H, CH$_2$OH), 2.0-1.65 (mc, 4H, CH$_2$CH$_2$), 1.44 (s, 9H, NHCO$_2$C(CH$_3$)$_3$) ppm.

$^{13}$C-NMR (75 MHz, CDCl$_3$), δ: 170.6 (CONHPh), 156.2 (C(CH$_3$)$_3$), 137.7 (NHCO$_2$), 128.9 (C$_{Ar}$—H$_b$), 124.3 (C$_{Ar}$—H$_c$), 119.9 (C$_{Ar}$—H$_a$), 62.4 (CH$_2$OH), 54.6 (CHNHBoc), 30.1 (CH$_2$CH$_2$), 28.3 (NHCO$_2$C(CH$_3$)$_3$), 28.0 (CH$_2$CH$_2$) ppm.

MS: Positive mode [M+H]$^+$=309, [M+Na]$^+$=331.

MS: Negative mode [M−H]$^-$=307.

Example 3

Preparation of Intermediate [8a]: 4-(tert-butoxycarbonylamino)-5-oxo-(phenylamino)Pentyl Methanesulfonate

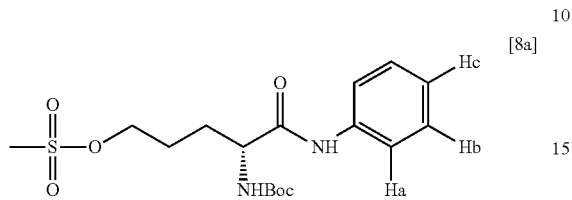
[8a]

To a stirred solution of compound [7a] (0.98 g, 3.19 mmol) in 10 ml anhydrous CH$_2$Cl$_2$ was added 0.66 ml of anhydrous Et$_3$N (4.76 mmol, 1.48 eq) at 0° C. To this solution was added MsCl (3.86 mmol, 1.21 eq) and the mixture was stirred for 2 h at 0° C. After then, the crude was evaporated to dryness, and filtered over SiO$_2$ using AcOEt as the eluant. Once the filtered was evaporated, finally it was crystallized in acetone at 0° C., yielding 1.12 g (91%) of the desired product.

$^1$H-NMR (300 MHz, CDCl$_3$): δ 8.435 (s, 1H), 7.512 (dd, J$_1$=7.8 Hz, J$_2$=8.4 Hz, 2H), 7.293 (t, J=8.4 Hz, 2H), 7.091 (t, J=7.5 Hz, 1H), 5.375 (d, J=8.4 Hz, 1H), 4.4 (m, 1H), 4.306 (m, 2H), 3.302 (s, 3H), 2.095-1.750 (m, 4H), 1.446 (s, 9H) ppm.

$^{13}$C-NMR (300 MHz, CDCl$_3$): δ 170.03, 156.15, 137.63, 128.93, 124.41, 119.83, 69.18, 53.67, 37.46, 28.84, 28.28, 25.34 ppm.

MS: Positive mode [M+Na]$^+$=409.
MS: Negative mode [M+2H$_2$O−H]$^−$=421.

Example 4

Preparation of Intermediate [9a]: tert-butyl-2-oxo-1-phenylpiperidin-3-ylcarbamate

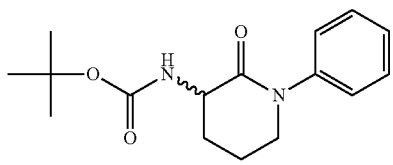
[9a]

Under inert atmosphere, LDA (1.04 mmol, 2 eq) was added to a solution of compound [8a] (0.200 g, 0.52 mmol) in anhydrous THF (5 ml) at 0° C. The solution was stirred for 2.5 h, warming to room temperature. After then, the crude was evaporated to dryness, and purified over Al$_2$O$_3$ using Hexane/AcOEt from 70/30 to 50/50 as the eluant, yielding 0.09 g (60%) of the desired product [9a] and 0.60 g (40%) of the by-product [10a].

$^1$H-NMR (400 MHz, CDCl$_3$): δ 7.39 (t, J=7.6 Hz, 2H$_{Ar}$), 7.25 (m, 3H$_{Ar}$), 5.5 (br, 1H, NHBoc), 4.26 (m, 1H, CHNHBoc), 3.71 (m, 2H, —CHCH$_2$CH$_2$CH$_2$—), 2.61 (m, 1H, CHCH$_2$CH$_2$CH$_2$—), 2.04 (m, 2H, —CHCH$_2$CH$_2$CH$_2$—), 1.71 (m, 1H, CHCH$_2$CH$_2$CH$_{12}$—), 1.46 (s, 9H, $^t$Bu) ppm.

$^{13}$C-NMR (400 MHz, CDCl$_3$): δ 169.94 (CONH), 155.94 (OCONH), 142.47 (C$_q$, C$_{Ar}$), 129.15 (CH, C$_{Ar}$), 126.81 (CH, C$_{Ar}$), 125.64 (CH, C$_{Ar}$), 79.622 (C$_q$, $^t$Bu), 51.90 (—CHCH$_2$CH$_2$CH$_2$—), 50.14 (—CHCH$_2$CH$_2$CH$_2$—), 28.36 (CH$_3$, $^t$Bu), 27.39 (—CHCH$_2$CH$_2$CH$_2$—), 21.14 ppm (—CHCH$_2$CH$_2$CH$_2$—).

MS: Positive mode [M+H]$^+$=291, [M+Na]$^+$=313.

Example 5

Preparation of Intermediate [10a]: Tert-butyl-2-(phenylcarbamoyl)-pyrrolidine-1-carboxylate

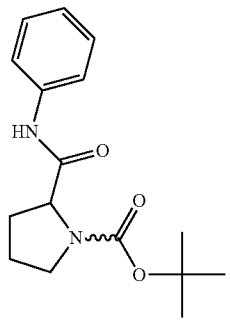
[10a]

Under inert atmosphere, $^t$BuOK (0.070 g, 0.65 mmol) was added to a solution of compound [8a] (0.250 g, 0.65 mmol) in anhydrous THF (5.8 ml). The reaction mixture was heated up to 50° C. during 1 h. After then, the crude was evaporated to dryness, and purified over SiO$_2$ using Hexane/AcOEt 50/50 as the eluant, yielding 0.183 g (97%) of the desired product [10a].

$^1$H-NMR (300 MHz, CDCl$_3$): δ 9.5 (br, NHPhe), 7.51 (dd, J$_1$=8.9 Hz, J$_2$=1.2 Hz, 2H$_{Ar}$), 7.31 (t, J=7.8 Hz, 2H$_{Ar}$), 7.08 (t, J=7.2 Hz, 1H$_{Ar}$), 4.4 (br, 1H, CH), 3.4 (br, 2H, CH$_2$), 1.93 (m, 2H, CH$_2$), 1.49 (s, 9H, $^t$Bu), 1.49 (s, 2H, CH$_2$) ppm.

MS: Positive mode [M+H]$^+$=291, [M+Na]$^+$=313.
MS: Negative mode [M−H]$^−$=289, [M+2H$_2$O−H]$^−$=325.

Example 6

Preparation of Intermediate [11a]

[11a]

To a stirred solution of [9a] (0.08 g, 0.28 mmol) in 1.5 ml of CH$_2$Cl$_2$ was added 0.50 ml of trifluoroacetic acid at room temperature, and the mixture was sealed and stirred for 0.5 h. After then, the crude was evaporated to dryness, yielding an orange oily residue of the organic salt [11a], which was precipitated using $^iPr_2O$. The remaining solid was used without further purification.

Example 7

Preparation of Intermediate [12a]

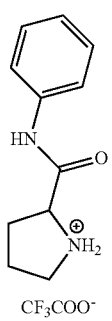

[12a]

To a stirred solution of [10a] (0.90 g, 3.11 mmol) in 13 ml of $CH_2Cl_2$ was added 5.5 ml of trifluoroacetic acid at room temperature, and the mixture was sealed and stirred for 1 h. After then, the crude was evaporated to dryness, yielding an orange oily residue of the organic salt [12a], which was used without further purification.

Example 8

Preparation of N-(2-oxo-1-phenylpiperidin-3-yl)Benzenesulfonamide

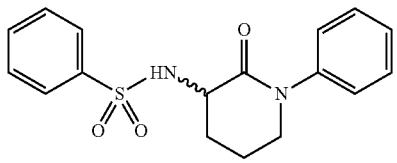 [SMILES: O=C1C(NS(=O)(=O)c2ccccc2)CCCN1c1ccccc1]

Under inert atmosphere, to a stirred solution of compound [12a] (0.093 g, 0.29 mmol) in 1 ml anhydrous DMF at 0° C. was added anhydrous $Et_3N$ (0.15 ml, 1.04 mmol). This mixture was stirred for 5 min, and then $PhSO_2Cl$ (0.06 ml, 0.44 mmol) was added at 0° C. The reaction was stirred for 2 h at this temperature. Then, the solvent was removed and the crude was chromatographically purified over $SiO_2$ using Hexane/AcOEt 50/50 as the eluant, yielding 0.057 g (63%) of the desired product.

$^1$H-NMR (300 MHz, $CDCl_3$): δ 7.92 (dd, $J_1$=8.1 Hz, $J_2$=1.5 Hz, $2H_{Ar}$), 7.6-7.48 (m, $3H_{Ar}$), 7.37 (dd, $J_1$=7.8 Hz, $J_2$=7.2 Hz, $2H_{Ar}$), 7.26 (tt, $J_r$=8.1 Hz, $J_2$=~1 Hz, $1H_{Ar}$), 7.16 (dd, $J_1$=8.1 Hz, $J_2$=1.5 Hz, $1H_{Ar}$), ~6 (s, 1H, $NHSO_2$), 3.8-3.54 (mc, 3H, 1×$CHCH_2CH_2CH_2$—N+2×$CHCH_2CH_2CH_2$—N), 2.61 (m, 1H, =$CHCH_2CH_2CH_2$—N), 2.1-1.8 (mc, 3H, 1×C$\underline{H}CH_2CH_2CH_2$—N+2×—$CHCH_2CH_2CH_2$—N) ppm.

MS: Positive mode $[M+H]^+$=331, $[M+Na]^+$=353.

Example 9

Preparation of N-(2-oxo-1-phenylpiperidin-3-yl) Naphthalene-2-sulfonamide

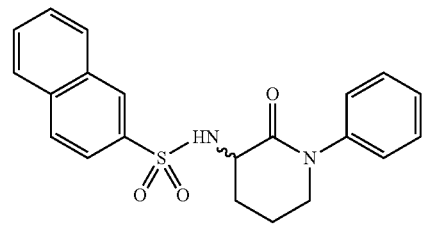 [SMILES: O=C1C(NS(=O)(=O)c2ccc3ccccc3c2)CCCN1c1ccccc1]

Following a procedure analogous to that described in Example 8, the title compound was obtained as a white solid in 62% yield.

MS: Positive mode $[M+H]^+$=380, $[M+Na]^+$=403.

Example 10

Preparation of N-(2-oxo-1-phenylpiperidin-3-yl) Quinoline-8-sulfonamide

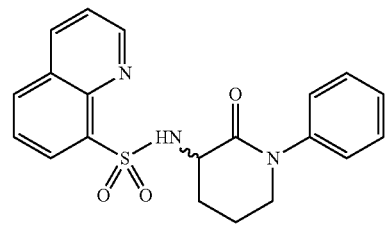 [SMILES: O=C1C(NS(=O)(=O)c2cccc3cccnc23)CCCN1c1ccccc1]

Following a procedure analogous to that described in Example 8, the title compound was obtained as a white solid in 63% yield.

MS: Positive mode $[M+H]^+$=382, $[M+Na]^+$=404.

Example 11

Preparation of 4-Chloro-N-(2-oxo-1-phenylpiperidin-3-yl) Benzene-sulfonamide

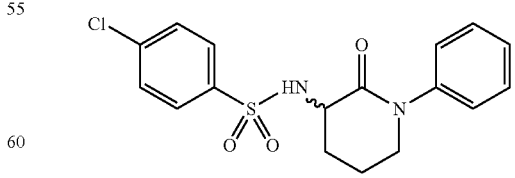

Following a procedure analogous to that described in Example 8, the title compound was obtained as grey oil in 90% yield.

MS: Positive mode $[M+H]^+$=365, $[M+Na]^+$=387.

Example 12

Preparation of 5-(Dimethylamino)-N-(2-oxo-1-phenylpiperidin-3-yl)-naphthalene-1-sulfonamide

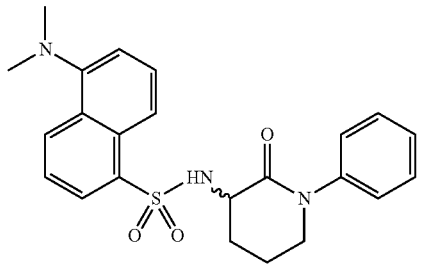 [SMILES: CN(C)c1cccc2c(S(=O)(=O)NC3CCCN(c4ccccc4)C3=O)cccc12]

Following a procedure analogous to that described in Example 8, the title compound was obtained as yellow oil in 80% yield.

MS: Positive mode: [M+H]$^+$=424, [M+Na]$^+$=446.

Example 13

Preparation of 5-Chloro-N-(2-oxo-1-phenylpiperidin-3-yl)Thiophene-2-sulfonamide

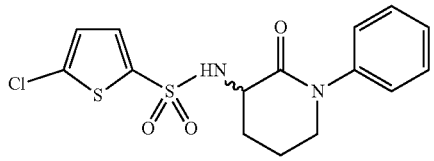 [SMILES: O=C1C(NS(=O)(=O)c2ccc(Cl)s2)CCCN1c1ccccc1]

Following a procedure analogous to that described in Example 8, the title compound was obtained as white oil in 80% yield.

MS: Positive mode [M+H]$^+$=371, [M+Na]$^+$=393.

Example 14

Preparation of (E)-N-(2-oxo-1-phenylpiperidin-3-yl)-2-phenylethene-sulfonamide

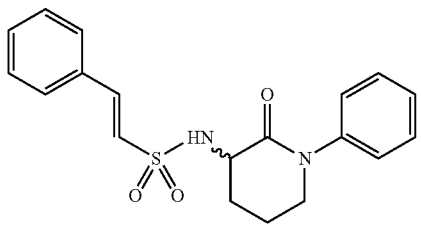 [SMILES: O=C1C(NS(=O)(=O)/C=C/c2ccccc2)CCCN1c1ccccc1]

Following a procedure analogous to that described in Example 1, the title compound was obtained as a white solid in 71% yield.

MS: Positive mode [M+H]$^+$=357, [M+Na]+=379.

Example 15

Preparation of N-benzyl-N-(2-oxo-1-phenylpiperidin-3-yl)-benzenesulfonamide

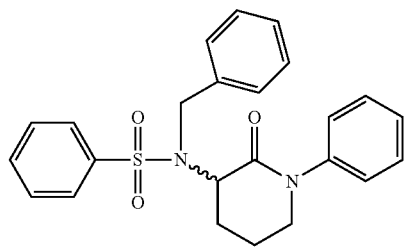 [SMILES: O=C1C(N(Cc2ccccc2)S(=O)(=O)c2ccccc2)CCCN1c1ccccc1]

Under inert atmosphere, to a stirred solution of NaH (2.5 mg, 0.05 mmol) in 0.10 ml anhydrous DMF at 0° C., was added a solution of compound of Example 8 (0.02 g, 0.05 mmol) in 0.20 ml anhydrous DMF. After 1.5 h at 0° C., benzyl bromide (7 μl, 0.05 mmol) was added to the reaction mixture. This mixture was stirred for 2 h, and then solvent was completely removed. The crude was chromatographically purified over SiO$_2$ using Hexane/AcOEt 50/50 as the eluant, yielding 0.016 g (71%, purity 92%) of the desired product.

$^1$H-NMR (300 MHz, CDCl$_3$): δ 7.92 (dd, J$_1$=8.1 Hz, J$_2$=1.5 Hz, 2H$_{Ar}$), 7.6-7.48 (m, 3H$_{Ar}$), 7.37 (dd, J$_1$=7.8 Hz, J$_2$=7.2 Hz, 4H$_{Ar}$), 7.26 (tt, J$_1$=8.1 Hz, J$_2$=~1 Hz, 2H$_{Ar}$), 7.16 (dd, J$_1$=8.1 Hz, J$_2$=1.5 Hz, 4H$_{Ar}$), 4.42 (sa, 2H, CH$_2$Ph), 3.8-3.54 (mc, 3H, 1×CHCH$_2$CH$_2$CH$_2$—N+2×CHCH$_2$CH$_2$CH$_2$—N), 2.61 (m, 1H, =CHCH$_2$CH$_2$CH$_2$—N), 2.1-1.8 (mc, 3H, 1×CHCH$_2$CH$_2$CH$_2$—N+2×—CHCH$_2$CH$_2$CH$_2$—N) ppm.

Example 16

Preparation of Benzyl 4-(tert-butoxycarbonylamino)-5-oxo-5-(N-(2-oxo-1-phenylpiperidin-3-yl)Phenylsulfonamido)Pentanoate

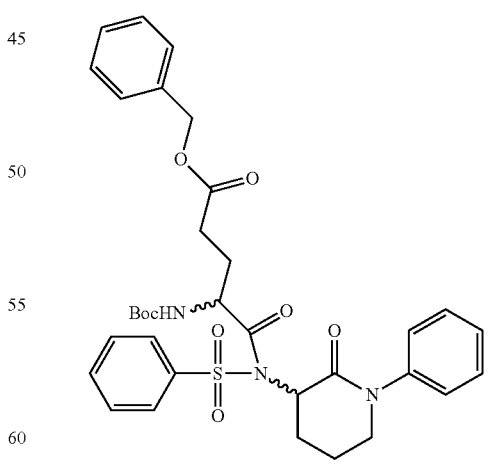

Step 1: Under inert atmosphere, to a stirred solution of NaH (3 mg, 0.07 mmol) in 0.10 ml anhydrous DMF at 0° C., was added a solution of compound of Example 8 (0.022 g, 0.06 mmol) in 0.20 ml anhydrous DMF. The temperature was maintained during 1.5 h.

Step 2: Under inert atmosphere in another reaction vessel, N,N'-Diisopropyl carbodiimide (12 μl, 0.08 mmol) was added to a solution of Boc-L-Glutamic acid-5-benzyl ester (0.022 g, 0.065 mmol) in 0.20 ml anhydrous DMF at room temperature. The temperature was maintained during 1.5 h.

Step 3: After 1.5 h, the reaction mixture of step 1 was added to reaction the reaction mixture of step 2 at room temperature, and was stirred during 6 h. Then solvent was completely removed. The crude was chromatographically purified over $Al_2O_3$ using Hexane/AcOEt 25/75 as the eluant, yielding 0.025 g (60%, purity 93%) of the desired product.

$^1$H-NMR (300 MHz, CDCl$_3$): δ 7.92 (dd, $J_1$=8.1 Hz, $J_2$=1.5 Hz, 2H$_{Ar}$), 7.6-7.48 (m, 3H$_{Ar}$), 7.37 (dd, $J_1$=7.8 Hz, $J_2$=7.2 Hz, 2H$_{Ar}$), 7.26 (tt, $J_1$=8.1 Hz, $J_2$=~1 Hz, 1H$_{Ar}$), ~7.20 (mc, 7H, 7×H$_{Ar}$), 5.35 (d, 1H, J=7.8 Hz, CHNHBoc), 5.04 (d, 2H, J=2.6 Hz, BnOCH$_2$), 4.26 (sa, 1H, CH$_2$C$\overline{\text{H}}$NHBoc), 3.8-3.54 (mc, 3H, 1×CHC$\overline{\text{H}}_2$CH$_2$CH$_2$—N+2×CHC$\overline{\text{H}}_2$CH$_2$CH$_2$—N), 2.2-1.8 (mc, 8H), 1.40 (s, 9H, NHCO$_2$C(CH$_3$)$_3$) ppm.

What is claimed is:

1. A compound having formula (I)

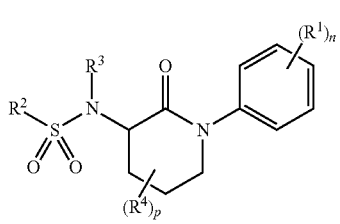

and the salts and stereoisomers thereof, wherein $R^1$ is hydrogen, nitro, cyano, azido, polyhaloC$_{1-6}$alkyl, and polyhaloC$_{1-6}$alkoxy;

$R^2$ is C$_{3-7}$cycloalkyl optionally substituted with C$_{1-6}$alkyl; C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

$R^3$ is hydrogen, C$_{1-6}$alkylcarbonyl, C$_{1-6}$alkyl optionally substituted with aryl, C$_{1-6}$alkoxy -C$_{1-6}$alkyl, or C$_{3-7}$cycloalkyl, C$_{1-6}$alkyl optionally substituted with Het;

$R^4$ is hydrogen, hydroxy, halo, nitro, cyano, carboxyl, C$_{1-6}$alkyl, C$_{1-6}$alkoxy, C$_{1-6}$alkoxy -C$_{1-6}$alkyl or C$_{3-7}$cycloalkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy, C$_{1-6}$alkyl optionally substituted with aryl or Het; C$_{3-7}$cycloalkyl optionally substituted with C$_{1-6}$alkyl; C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

n is one, two, three, four or five;

p is one, two, three, four or five, independently of n;

each aryl as a group or part of a group is phenyl or naphthalenyl, each optionally substituted with one, two or three substituents selected from halo, hydroxy, nitro, cyano, carboxyl, C$_{1-6}$alkyl, C$_{1-6}$alkoxy, C$_{1-6}$alkoxy C$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy; and each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, polyhaloC$_{1-6}$alkyl, polyhalo C$_{1-6}$alkoxy, and C$_{3-7}$cycloalkyl.

2. A compound according to claim 1, wherein $R^1$ is hydrogen, nitro, cyano, azido, polyhaloC$_{1-6}$alkyl, and polyhaloC$_{1-6}$alkoxy;

$R^2$ is C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl; Het; or —NR$^{4a}$R$^{4b}$, wherein R$^{4a}$ and R$^{4b}$ are, each independently, C$_{1-6}$alkyl, or R$^{4a}$ and R$^{4b}$ together with the nitrogen to which they are attached form a 5- or 6-membered saturated heterocyclic ring;

$R^3$ is hydrogen, C$_{1-6}$alkylcarbonyl, C$_{1-6}$alkyl optionally substituted with aryl, C$_{1-6}$alkoxy -C$_{1-6}$alkyl, or C$_{3-7}$cycloalkyl, C$_{1-6}$alkyl optionally substituted with Het;

$R^4$ is hydrogen;

n is one, two, three, four or five;

p is one;

each aryl as a group or part of a group is phenyl or naphthalenyl, each optionally substituted with one, two or three substituents selected from halo, hydroxy, nitro, cyano, carboxyl, C$_{1-6}$alkyl, C$_{1-6}$alkoxy, C$_{1-6}$alkoxy C$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy; and each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, polyhaloC$_{1-6}$alkyl, polyhaloC$_{1-6}$ alkoxy, and C$_{3-7}$ cycloalkyl.

3. A compound according to claim 1, wherein R$^1$ is hydrogen;

$R^2$ is C$_{1-6}$alkyl optionally substituted with C$_{3-7}$cycloalkyl, aryl or Het; C$_{2-6}$alkenyl optionally substituted with C$_{3-7}$cycloalkyl, aryl or Het; aryl and Het;

$R^3$ is hydrogen, C$_{1-6}$alkyl and C$_{1-6}$alkylcarbonyl;

$R^4$ is hydrogen;

n is one or two;

p is one;

each aryl as a group or part of a group is phenyl or naphthalenyl, each optionally substituted with one, two or three substituents selected from halo, hydroxy, nitro, cyano, carboxyl, C$_{1-6}$alkyl, C$_{1-6}$alkoxy, C$_{1-6}$alkoxy C$_{1-6}$alkyl, C$_{1-6}$alkylcarbonyl, amino, mono- or diC$_{1-6}$alkylamino, azido, mercapto, polyhaloC$_{1-6}$alkyl, and polyhaloC$_{1-6}$alkoxy; and each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo $C_{1-6}$alkyl, polyhalo $C_{1-6}$alkoxy, and $C_{3-7}$cycloalkyl.

4. A compound according to any one of claims 1-3, wherein
$R^1$ is hydrogen;
$R^2$ is $C_{2-6}$alkenyl optionally substituted with aryl or Het; aryl; or Het;
$R^3$ is hydrogen;
$R^4$ is hydrogen;
n is one or two;
p is one;
each aryl as a group or part of a group is phenyl or naphthalenyl, each optionally substituted with one or two substituents selected from halo, amino, mono- or di$C_{1-6}$alkylamino, and polyhalo$C_{1-6}$alkyl; and
each Het as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one or two substituents each independently selected from the group consisting of halo and polyhalo$C_{1-6}$alkyl.

5. A process for preparing a compound having formula (I)

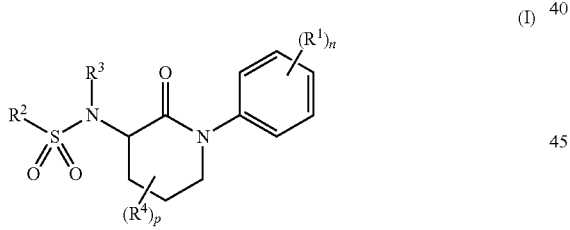

(I)

as claimed in claim 1, said process comprising the step of a) reacting in a suitable medium a compound of formula (II) with a compound of formula (III)

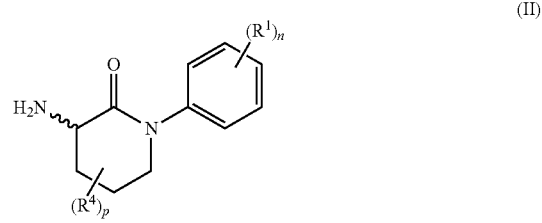

(II)

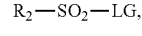

(III)

and b) optionally further comprising the step of reacting in a suitable medium the product of step a) with $R_3$—Y;

wherein $R_1, R_2, R_3, R_4$, n and p have the same definition as provided in of claim 1;

LG is an halogen atom;

Y is an activating group in coupling reactions or a leaving group in substitution reactions, wherein, in substitution reactions Y is an halogen atom;

wherein in coupling reactions Y is an activated carboxyl derivative, or an active ester, wherein the suitable medium of the reaction in step a) is anhydrous or non anhydrous chlorinated solvent, or a hydrous or anhydrous polar aprotic solvent, at a temperature between 0° C. and 40° C., wherein the suitable medium of the reaction in step b) is in the presence of an inorganic or organic base, at a temperature between −78° C. and 60° C., and wherein the reaction solvent is a polar aprotic solvent.

\* \* \* \* \*

UNITED STATES PATENT AND TRADEMARK OFFICE
CERTIFICATE OF CORRECTION

PATENT NO.         : 8,569,507 B2
APPLICATION NO.    : 13/332625
DATED              : October 29, 2013
INVENTOR(S)        : Josep Castells Boliart et al.

It is certified that error appears in the above-identified patent and that said Letters Patent is hereby corrected as shown below:

Title Page, Item (73) Assignee
    change "INSTITUT UNIV. DE CIÈNCIA I TECHNOLOGIA, S. A." to
    --INSTITUT UNIV. DE CIÈNCIA I TECNOLOGIA, S. A.--

Signed and Sealed this
Eleventh Day of February, 2014

Michelle K. Lee
*Deputy Director of the United States Patent and Trademark Office*